United States Patent [19]
Boxer

[11] 4,022,189
[45] May 10, 1977

[54] DEVICE AND PROCESSES FOR ALLEVIATION OF MUSCULAR PAIN AND STIFFNESS, AND SYMPTOMS OF NON-MUSCULAR AILMENTS

[76] Inventor: Steve Boxer, 13617 Sherman Way, Van Nuys, Calif. 91405

[22] Filed: May 30, 1975

[21] Appl. No.: 582,303

Related U.S. Application Data

[63] Continuation-in-part of Ser. No. 394,118, Sept. 4, 1973, Pat. No. 3,987,787.

[52] U.S. Cl. .............................. 128/1 R; 128/268
[51] Int. Cl.² .................. A61M 37/00; A61F 7/02
[58] Field of Search ................ 128/1 R, 1.3, 2.1 C, 128/268, 253

[56] References Cited

UNITED STATES PATENTS

| | | | |
|---|---|---|---|
| 272,904 | 2/1883 | Russell | 128/1.3 |
| 658,027 | 9/1900 | Steiger | 128/1.3 |
| 1,738,859 | 12/1929 | White | 128/1.3 |
| 3,625,202 | 12/1971 | Oyoshirhara | 128/24.3 |
| 3,886,939 | 6/1975 | Boxer | 128/268 |

*Primary Examiner*—Aldrich F. Medbery
*Attorney, Agent, or Firm*—John Joseph Hall

[57] ABSTRACT

A device and processes comprising the application of a device containing one or more small, rigid objects to produce pressure at designated points of a person's body without puncturing the person's skin, with the added feature of magnetization of the rigid objects to enhance the effectiveness of the device and processes.

26 Claims, 3 Drawing Figures

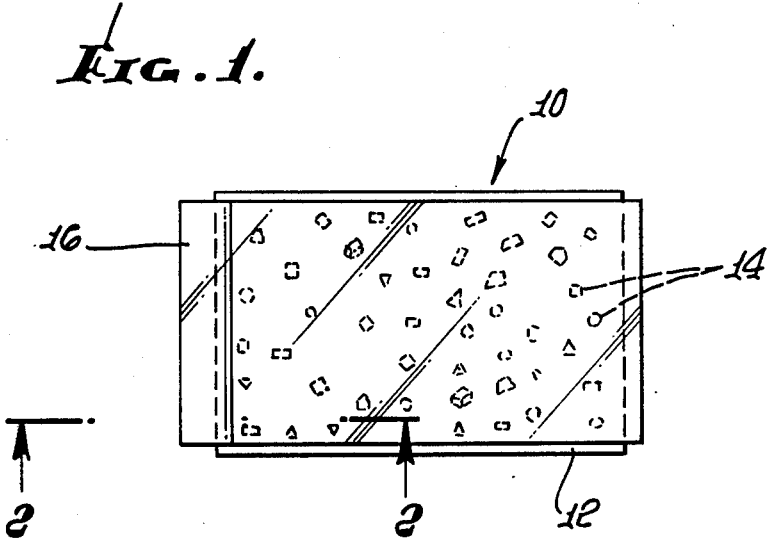
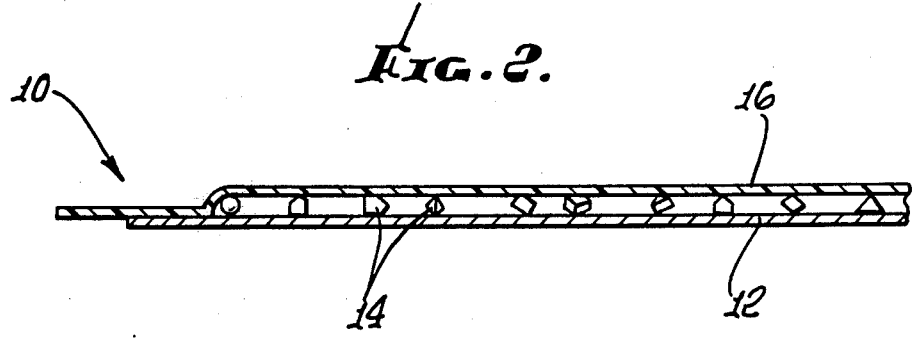
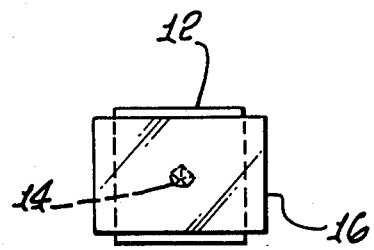

DEVICE AND PROCESSES FOR ALLEVIATION OF MUSCULAR PAIN AND STIFFNESS, AND SYMPTOMS OF NON-MUSCULAR AILMENTS

This application is a continuation in part of Application Ser. No. 394,118, filed Sept. 4, 1973, and now U.S. Pat. No. 3,987,787.

SUMMARY OF THE INVENTION

This invention comprises the affixation of one or more small, rigid objects of varying shape to an adhesive base material, such as conventional surgical tape or plaster, and the like. The size of the objects may vary from about one millimeter to about twelve millimeters. The objects may be made of any suitable rigid material with the capability of maintaining its rigidity under moderate pressure. The adhesive base material may be of any suitable size, preferably about one inch wide and about two inches long.

The device is used in a process for alleviating symptoms of non-muscular ailments and discomfort, including relief from habit problems by affixing a minimum of two of the small objects to one or more trigger points, motor points, reflex points, or acupuncture loci of a person's body, without puncturing the person's skin. This process comprises the application of a minimum of two of the small objects to trigger points, or to motor points, or to reflex points, or to acupuncture loci, or any combination thereof, of a person's body. The use of a minimum of two objects is critical. However, the minimum of two objects may be fulfilled by the use of a single device and two objects, or two devices each having one object.

The device is also used in a process for alleviating muscular pain and stiffness. This process comprises the application of a minimum of five small objects to the area of pain or stiffness of a person's body without puncturing the person's skin. The five or more small objects may be applied by means of a single device containing the objects, or by means of individual devices each having a single, small object, or various combinations. Use of a minimum of five small objects is critical.

Magnetization of the small objects enhances the effect of the devices and of the processes. The amount of magnetization of the small objects is preferably in the range of from 100 to 1000 gauss.

The device may be used in processes for a person's weight control and for control and reduction of smoking, by affixing a minimum of two of the small objects to one or more body trigger points or acupuncture loci or any combination thereof, without puncturing the person's skin. The use of a minimum of two objects is critical, but may be fulfilled by using single device with two objects, or two devices each having one object thereon.

It is, therefore, an object of this invention to provide a device for alleviation of muscular pain and stiffness, and symptoms of non-muscular ailments and discomfort, including relief from habit problems.

Another object of this invention is to provide a process for alleviation of muscular pain and stiffness.

A further object of this invention is to provide a process for alleviation of the symptoms of non-muscular ailments and discomfort, including habit problems.

A still further object of this invention is to provide processes and devices for alleviation of muscular pain and stiffness, and symptoms of non-muscular ailments and discomfort, which can be readily used by a person at relatively low cost.

These and other objects will be more readily understood by reference to the accompanying drawing, in which FIG. 1 is a plan view of embodiment of my invention.

FIG. 2 is a section taken along line 2—2 of FIG. 2.

FIG. 3 is an enlarged section of a portion of FIG. 1 showing an individual object.

The device 10 has a base material 12 having adhesive properties, such as surgical plaster and the like. A single, rigid object 14 is affixed to the base material 12. The device 10 may have one or a plurality of small objects 14 affixed to the base material 12. The plurality of objects 14 may be arranged at random on base material 12 or in a symmetrical arrangement without adversely affecting the operation of the device 10.

The small size of the objects 14 is critical but may vary from about one to about 12 millimeters in thickness. The objects 14 may vary in form and shape. Thus, the objects 14 may be rectangular, cubic, rhombic, or polygonal in form, or circular or irregularly shaped.

However, the objects 14 must be sufficiently rigid to maintain pressure on a person's body when applied to a body area, without substantial change in shape. If the foregoing requirement is met, the small objects 14 may be solid or hollow, and made from any suitable material.

A device 10 may contain one or more small objects 14 which may be all the same shape, that is, rectangular, or each of the objects 14 may be of a different shape from the other, or any combination of shapes, without adversely affecting the operation of the device 10 or the results of the processes.

A cover 16 of any suitable material may be placed over the small objects 14, but is not necessary.

To increase the effectiveness of the device 10 and the processes in which it is used, the small objects 14 may be made from a material which can be magnetized. A preferable amount of magnetization for the small objects 14 is from 100 to 1000 gauss. The magnetization may be performed by any suitable means.

As used for the alleviation of muscular pain and stiffness, the device 10 is applied to a person's body in such a way that at least five of the small objects 14 are affixed to the area of muscular pain and stiffness, without puncturing the person's skin. The small objects 14 are kept in position for a suitable length of time, ranging from one hour on up to one or more days, to produce alleviation of muscular pain and stiffness.

For the alleviation of the symptoms of non-muscular ailments and discomfort, including relief from habit conditions, at least two of the small objects 14 are applied to at least one or more areas of a person's body selected from the group consisting of body trigger points, motor points, reflex points, and acupuncture loci, without puncturing the person's skin. The two or more small objects 14 may be placed on the same base material 12, or on separate pieces of base material 12, or any combination of the foregoing. The time of application of the two or more objects 14 may range from a period of about one hour on up to one day or more, with a resulting alleviation of the symptoms of nonmuscular ailments and discomfort.

In processes for a person's weight control, and control and reduction of smoking, at least two of the small objects 14 are applied to at least one or more areas of a person's body selected from the group consisting of acupuncture loci and body trigger points, without puncturing the person's skin. The two or more small objects 14 may be placed on the same base material 12, or on separate pieces of base material 12. The time of application of the two or more objects 14 may range from a period of about one hour on up to one day or more. Use of the foregoing processes will control a person's weight as well as control a person's smoking and reduction of smoking.

Although I have described my invention in detail with reference to the accompanying drawing illustrating preferred embodiments of my invention and with reference to preferred embodiments of processes, it is understood that numerous changes in the details of construction and arrangement of parts, and in the steps of the processes, may be made without departing from the spirit and scope of the invention as hereinafter claimed.

I claim:

1. A device for alleviating the symptoms of nonmuscular ailments and discomfort of a person's body, by applying said device to at least two body locations selected from the group consisting of body trigger points, motor points, reflex points, and acupuncture loci, without easily puncturing said person's skin, comprising:
    a base material having non-medicated adhesive properties, and
    at least one small rigid object affixed to one side of said base material, said object being located between said base material and the person's body location.

2. A device according to claim 1 in which said object has a thickness ranging from about 1 millimeter to about 12 millimeters.

3. A device according to claim 1 in which said rigid object is magnetized.

4. A device for alleviating muscular pain and stiffness of a person's body by applying said device to the body area having muscular pain and stiffness, without easily puncturing said person's skin, comprising:
    a base material having non-medicated adhesive properties, and at least five small, rigid objects affixed to one side of said base material, said objects being located between said base material and the person's body area.

5. A device according to claim 4 in which said small objects have a thickness ranging from about 1 millimeter to about 12 millimeters.

6. A device according to claim 4 in which said small objects are magnetized.

7. A device for alleviating muscular pain and stiffness of a person's body by applying a sufficient number of said devices to produce a minimum of five small, rigid objects pressing against the body area having muscular pain and stiffness, without easily puncturing said person's skin, comprising:
    a base material having non-medicated adhesive properties, and
    at least one small, rigid object affixed to one side of said base material, said objects being located between said base material and the said body area.

8. A device according to claim 7 in which said object has a thickness ranging from about 1 millimeter to about 12 millimeters.

9. A device according to claim 7 in which said object is magnetized.

10. A process for alleviating the symptoms of nonmuscular ailments and discomfort of a person's body by applying a device consisting of non-medicated adhesive material with at least one small, rigid object affixed to one side of said adhesive material in contact producing a pressure to at least two body locations selected from the group consisting of body trigger points, motor points, reflex points, and acupuncture loci, without puncturing said person's skin, and
    maintaining said device in position for a suitable length of time.

11. A process according to claim 10 in which said device is maintained in position for at least 1 hour.

12. A process according to claim 10 in which the small, rigid object of said device has a thickness ranging from about 1 to about 12 millimeters.

13. A process according to claim 10 in which at least one small, rigid object of said device is magnetized.

14. A process for alleviating muscular pain and stiffness of a person's body by
    applying a device consisting of non-medicated adhesive material with at least five small, rigid objects affixed to one side of said adhesive material in contact producing pressure at the area of muscular pain and stiffness without puncturing said person's skin, and
    maintaining said device in position for a suitable length of time.

15. A process according to claim 14 in which said device is maintained in position for at least 1 hour.

16. A process according to claim 14 in which said device has objects with a thickness ranging from about 1 millimeter to about 12 millimeters.

17. A process according to claim 14 in which at least one of said objects is magnetized.

18. A process for alleviating muscular pain and stiffness of a person's body by
    applying a sufficient number of devices, each having at least one small, rigid object, to produce a minimum of five small, rigid objects in contact producing pressure at the area of muscular pain and stiffness without puncturing said person's skin, and
    maintaining each of said devices in position for a suitable length of time.

19. A process according to claim 18 in which said devices are maintained in position for at least one hour.

20. A process according to claim 18 in which said objects have a thickness ranging from about one millimeter to about twelve millimeters.

21. A process according to claim 18 in which at least one of said objects is magnetized.

22. A device for weight control of excess weight of a person's body by applying said device to at least two body locations selected from the group consisting of body trigger points and acupuncture loci without puncturing the person's skin, comprising:
    a base material having non-medicated adhesive properties, and
    at least one small, rigid object affixed to one side of said base material, said object being located between said base material and the person's body location.

23. A device according to claim 1 in which said object has a thickness ranging from about 1 millimeter to about 12 millimeters.

24. A process for weight control of excess weight of a person's body, comprising:
    applying a device consisting of non-medicated adhesive material with at least one small, rigid object affixed to said non-medicated adhesive material in contact producing pressure to at least two body locations selected from the group consisting of body trigger points and acupuncture loci without puncturing said person's skin, and maintaining said device in position for a suitable length of time.

25. A process according to claim 24 in which said device is maintained in position for at least 1 hour.

26. A process according to claim 24 in which said small, rigid object of said device has a thickness ranging from about 1 to about 12 millimeters.

* * * * *